(12) United States Patent
Sundet et al.

(10) Patent No.: US 12,109,081 B2
(45) Date of Patent: Oct. 8, 2024

(54) MEDICAL DEVICE INSPECTION SCOPE

(71) Applicant: CLARUS MEDICAL, LLC, Minneapolis, MN (US)

(72) Inventors: Scott Allen Sundet, Edina, MN (US); Cindy Trosen Sundet, Edina, MN (US); Randal Alan Gatzke, Minneapolis, MN (US); Mark Brown, Minneapolis, MN (US)

(73) Assignee: Clarus Medical, LLC, Minneapolis, MN (US)

( * ) Notice: Subject to any disclaimer, the term of this patent is extended or adjusted under 35 U.S.C. 154(b) by 1052 days.

(21) Appl. No.: 16/351,106

(22) Filed: Mar. 12, 2019

(65) Prior Publication Data
US 2019/0282327 A1 Sep. 19, 2019

Related U.S. Application Data

(60) Provisional application No. 62/643,856, filed on Mar. 16, 2018.

(51) Int. Cl.
*A61B 90/70* (2016.01)
*A61B 1/06* (2006.01)
(Continued)

(52) U.S. Cl.
CPC ............ *A61B 90/70* (2016.02); *A61B 1/0661* (2013.01); *A61B 1/07* (2013.01); *A61B 90/361* (2016.02);
(Continued)

(58) Field of Classification Search
CPC ................ A61B 1/07; A61B 2090/306; A61B 2090/701
See application file for complete search history.

(56) References Cited

U.S. PATENT DOCUMENTS 4,860,094 A 8/1989 Hibino et al.
4,951,135 A 8/1990 Sasagawa
(Continued)

FOREIGN PATENT DOCUMENTS

JP H08-24211 1/1996
JP 2005270142 A 10/2005
(Continued)

OTHER PUBLICATIONS

"Bioprinter with Blue-Light Disinfection Minimizes Need for Cleanrooms," Medical Device and Diagnotic Industry [Online]. Retreived from the Internet: URL: www.mddionline.com/3d-printing/bioprinter-blue-light-disinfection-minimizes-need-cleanrooms, published Dec. 31, 2021, 2 pages.

*Primary Examiner* — Natasha N Campbell
(74) *Attorney, Agent, or Firm* — Merchant & Gould P.C.

(57) ABSTRACT

A medical device inspection scope may include a cylindrical outer layer having a diameter of less than 2 millimeters or even less than 1 millimeter, a cylindrical inner layer disposed concentrically within the outer layer, a circumferential space between the outer layer and the inner layer, and an inner lumen formed by the inner layer. The scope also includes multiple light transmitting fibers disposed in the circumferential space and a camera module disposed in the inner lumen. The light fibers may be designed to transmit illumination light and ultraviolet light. The scope may also optionally include a stiffening member.

16 Claims, 2 Drawing Sheets

(51) Int. Cl.
  *A61B 1/07* (2006.01)
  *A61B 90/00* (2016.01)
  *A61L 2/10* (2006.01)
  *A61L 2/28* (2006.01)
  *A61M 25/00* (2006.01)
  *F21V 33/00* (2006.01)
  *A61B 90/30* (2016.01)
  *F21W 131/20* (2006.01)

(52) U.S. Cl.
  CPC .............. *A61L 2/10* (2013.01); *A61L 2/28* (2013.01); *F21V 33/0068* (2013.01); *A61B 2090/306* (2016.02); *A61B 2090/373* (2016.02); *A61B 2090/701* (2016.02); *A61B 2090/702* (2016.02); *A61L 2202/11* (2013.01); *A61L 2202/14* (2013.01); *A61L 2202/24* (2013.01); *A61M 2025/0019* (2013.01); *A61M 2209/02* (2013.01); *F21W 2131/20* (2013.01)

(56) References Cited

U.S. PATENT DOCUMENTS

| | | | |
|---|---|---|---|
| 5,335,662 A | 8/1994 | Kimura | |
| 5,626,595 A | 5/1997 | Sklar et al. | |
| 5,833,683 A * | 11/1998 | Fuller | A61B 18/22 606/17 |
| 8,593,626 B2 | 11/2013 | Brouwer | |
| 8,933,416 B2 | 1/2015 | Arcand et al. | |
| 9,354,182 B2 | 5/2016 | Rochette et al. | |
| 10,245,339 B2 | 4/2019 | Shin et al. | |
| 10,279,058 B2 | 5/2019 | Lin et al. | |
| 10,543,058 B2 | 1/2020 | Bauco et al. | |
| 10,705,020 B2 | 7/2020 | Baribeau | |
| 10,709,313 B2 | 7/2020 | Stephenson | |
| 2004/0064019 A1 | 4/2004 | Chang et al. | |
| 2005/0157168 A1 | 7/2005 | Kaneko | |
| 2008/0159908 A1 * | 7/2008 | Redmond | A61L 2/10 422/24 |
| 2009/0099420 A1 | 4/2009 | Woodley et al. | |
| 2010/0217080 A1 * | 8/2010 | Cheung | A61B 1/00135 600/121 |
| 2012/0059255 A1 | 3/2012 | Paul et al. | |
| 2012/0071895 A1 | 3/2012 | Stahler et al. | |
| 2013/0008233 A1 | 1/2013 | Kosugi | |
| 2015/0012021 A1 | 1/2015 | Mihara | |
| 2015/0182106 A1 * | 7/2015 | King | A61B 1/043 600/431 |
| 2015/0231287 A1 | 8/2015 | Lin et al. | |
| 2015/0272426 A1 | 10/2015 | Narita | |
| 2016/0088999 A1 | 3/2016 | Langell | |
| 2016/0089001 A1 | 3/2016 | Hara et al. | |
| 2016/0353973 A1 * | 12/2016 | Mirza | A61B 17/320016 |
| 2017/0035277 A1 * | 2/2017 | Kucharski | A61B 1/018 |
| 2019/0038789 A1 | 2/2019 | Kang et al. | |
| 2019/0038791 A1 | 2/2019 | Gerrans et al. | |
| 2019/0224357 A1 | 7/2019 | Sundet | |
| 2019/0246884 A1 | 8/2019 | Lu | |
| 2019/0247050 A1 | 8/2019 | Goldsmith | |
| 2019/0290104 A1 | 9/2019 | Culman et al. | |
| 2019/0357751 A1 | 11/2019 | Friedlander et al. | |
| 2019/0357753 A1 | 11/2019 | Shigehisa | |
| 2021/0213148 A1 | 7/2021 | Gerrans et al. | |
| 2021/0339297 A1 | 11/2021 | Stephenson | |
| 2021/0386443 A1 | 12/2021 | Heimberger | |
| 2022/0080469 A1 | 3/2022 | Sundet et al. | |
| 2023/0233724 A1 | 7/2023 | Sundet et al. | |

FOREIGN PATENT DOCUMENTS

| | | | |
|---|---|---|---|
| WO | WO-2017034908 A1 * | 3/2017 | ............ A61B 90/70 |
| WO | WO2020023778 A1 | 1/2020 | |
| WO | WO2020096888 A1 | 5/2020 | |
| WO | WO2020096889 A1 | 5/2020 | |
| WO | WO2020096890 A1 | 5/2020 | |
| WO | WO2020096891 A1 | 5/2020 | |
| WO | WO2020096892 A1 | 5/2020 | |
| WO | WO2020096893 A1 | 5/2020 | |
| WO | WO2020096894 A1 | 5/2020 | |
| WO | WO2020123679 A1 | 6/2020 | |

* cited by examiner

MEDICAL DEVICE INSPECTION SCOPE

CROSS-REFERENCE TO RELATED APPLICATIONS

This application claims the benefit of U.S. Provisional Patent Application No. 62/643,856, filed Mar. 16, 2018, entitled, "Medical Device Inspection Scope." The disclosure of this priority application is hereby incorporated by reference in its entirety into the present application.

TECHNICAL FIELD

This application is directed to medical devices, systems and methods. More specifically, the application is directed to a scope for facilitating the inspection of medical devices.

BACKGROUND OF THE INVENTION

Millions of medical devices are used in hospitals throughout the world every day. With the continuing advancement of medical and surgical procedures over time, one of the trends is toward minimally invasive procedures performed through smaller incisions or even through the body's natural orifices. Examples of this trend include arthroscopic surgery, transcatheter aortic valve replacement ("TAVR"), natural orifice transluminal endoscopic surgery ("NOTES"), robotic surgery and many others. Many of these procedures involve the use of long, flexible catheter instruments and/or long, flexible endoscopes for visualizing the procedure. Additionally, endoscopes are used in countless different diagnostic and therapeutic procedures in many parts of the body.

One of the challenges with the use of endoscopes, fiber scopes, catheter-based medical/surgical instruments and other long, thin, reusable instruments is how to properly and effectively clean them. Many endoscopes and other instruments are too expensive to be disposable and so must be reused. Long, small-diameter, flexible instruments can be extremely hard to clean on the inside. They are also hard to inspect on the inside. Not only can flexible instruments collect bacteria and other contaminants, but they can also crack or become otherwise permanently deformed during use, for example when the instrument is bent or kinked. These instruments are typically processed in a cleaning facility located within the hospital, by workers with very little training. One way to inspect the inside of such instruments is to advance a small, flexible scope through the lumen(s) of the device, so that contaminants and damage can be seen. It can be difficult, however, for the person doing the inspection to effectively identify contaminants and internal damage to the device. Thus, the inspection process can be labor intensive and sometimes ineffective. It can also be hard to find a scope small enough to fit through the lumens of some medical devices while allowing for adequate visualization. Additionally, once contamination of an endoscope or catheter lumen (or similar inner portion of a medical device) is identified, it can often be difficult to adequately clean the lumen.

Therefore, it would be desirable to have improved devices, systems and methods for inspecting and possibly even disinfecting medical devices, specifically endoscopes, catheters and other long, thin, flexible medical devices that are difficult to inspect on the inside. At least some of these objectives are addressed in this application.

DETAILED DESCRIPTION OF THE INVENTION

Disclosed in this application are various examples of an endoscope (or simply "scope"), which may be used for inspecting the inside of medical devices or for any other suitable purpose. For example, the scope may be inserted into a lumen of a larger endoscope and advanced through the lumen to detect imperfections, damage, contamination and/or the like inside of the endoscope. In this way, the scope described in this application may help a user inspect a medical device that is being cleaned, sterilized or otherwise processed for reuse. In some embodiments, the scope may be designed not only to help visualize imperfections and contamination of a medical device lumen but also to disinfect or otherwise clean the lumen. These concepts and many others are described in greater detail below. The examples of various features and embodiments of the scope described below are not intended to limit the scope of the invention but are provided for descriptive purposes only.

Figure 1:
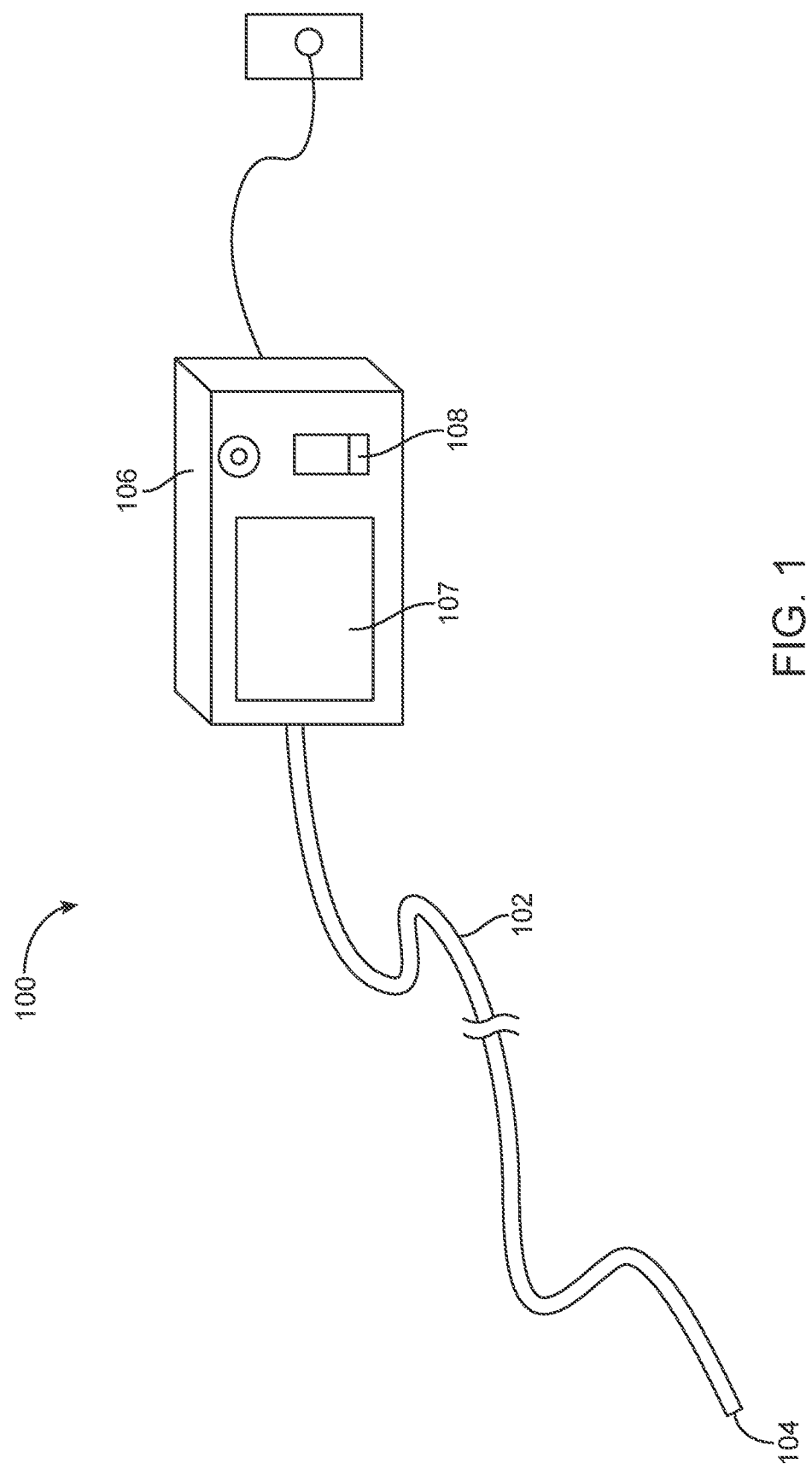
FIG. 1 is a perspective view of a medical device inspection scope, according to one embodiment.

Referring now to FIG. 1, in one example, an elongate, medical device inspection scope 100 includes an outer layer 102 (or "outer housing") and a distal end 104. The proximal end of the scope 100 is attached to a camera body/light source 106, which may sometimes be referred to as a "box." In some embodiments, the outer layer 102 of the scope 100 may have a specific diameter, sized to be able to fit within lumens of various endoscopes, catheters and/or other medical devices for inspection purposes. For example, in various embodiments, the outer layer 102 may have an outer diameter of less than 2 millimeters, and in some embodiments less than 1 millimeter.

In one embodiment, the camera body/light source 106 may include a display 107 and one or more controllers 108. The display 107 may display an image of the inside of the medical device being examined, or it may display data related to the inside of the medical device and/or the scope 100. In some embodiments, the camera body/light source 106 may connect to a separate display monitor for displaying images captured by the scope 100. The controllers 108 may include an on/off power switch and any other switch, knob, controller or the like.

In some embodiments, the scope 100 is configured to (1) emit illuminating light and capture still and/or video images of the inside of a medical device and (2) emit UV light (such as but not limited to UVC light) to clean/disinfect the inside/lumen of the medical device. Such an embodiment may be configured such that the user can switch back and forth between visible/illumination light and UVC light emission, and/or the user may in some cases emit both types of light simultaneously. In such embodiments, the controllers 108 may include a function control switch, button, knob or the like, for switching back and forth between illumination mode, UVC light mode and in some examples a combination light mode. In one embodiment, the light selection controller 108 may be a mechanical switch that allows the operator to toggle between visible/illumination light and UVC light. The switch may be rotary or leveler action and may be hand or foot operated. In another embodiment, the controller 108 may be an electronically activated switch, such as an electronic button on the display 107 or another screen, to switch between visible and UVC light. Embedded software, for example residing in the light source/box 106, may be configured to control the UVC energy dwell time (on/off/pulsed—e.g., the amount of energy delivered over a specific time period) and intensity. In one embodiment, a connector (not shown) splices the two different inputs (i.e., the visible light and the UVC light) into one single output, while preventing the individual light energies from escaping and while withstanding the caustic nature of UVC light. In one embodiment, both wavelengths enter a housing through a standard connection point (not shown) and are then spliced into one exit point. In various examples, any suitable splice connector may be used.

Figure 2:
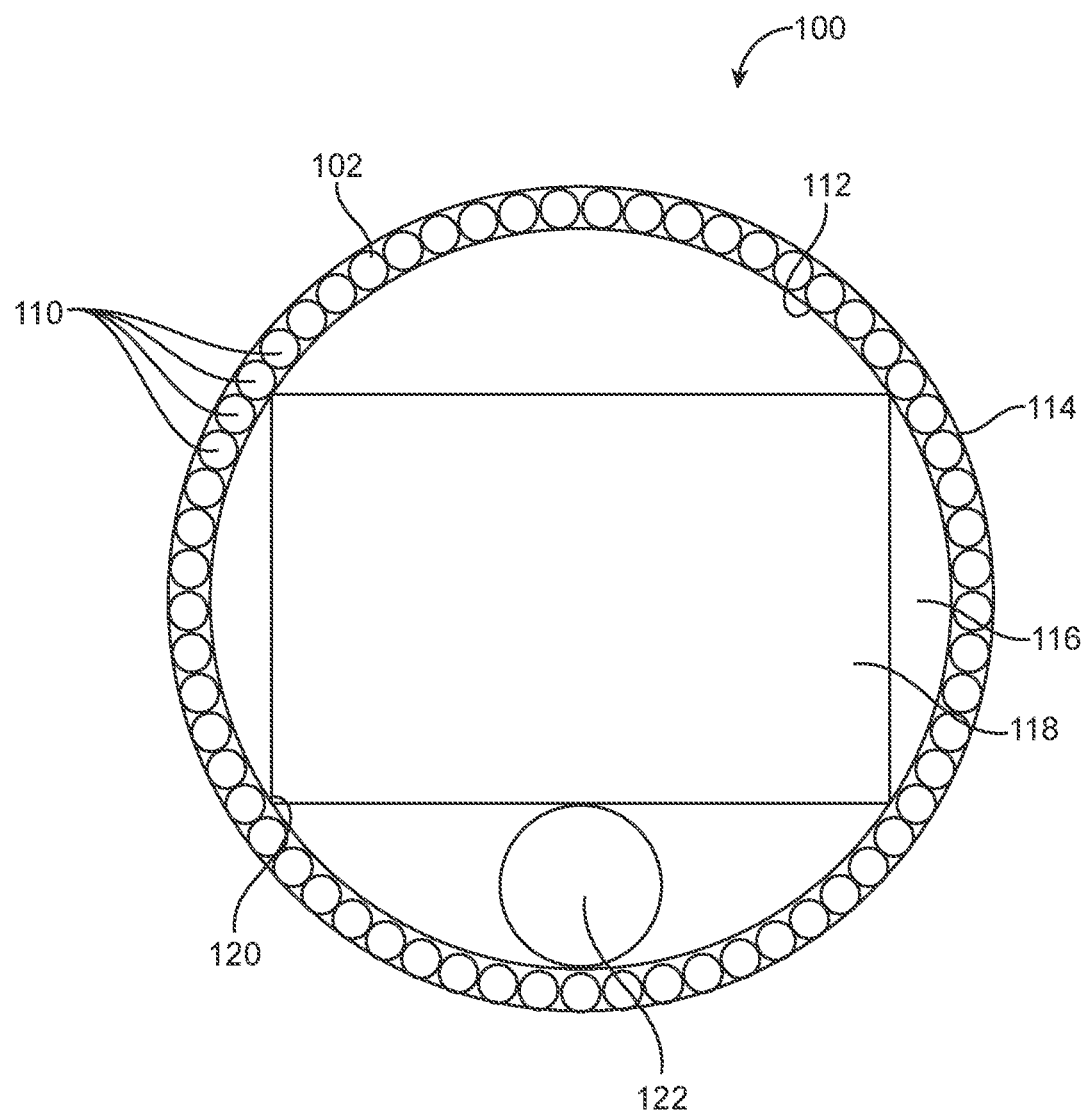
FIG. 2 is a cross-sectional view of the inspection scope of FIG. 1.

Referring to FIG. 2, the scope 100 of FIG. 1 is illustrated in cross section. As seen in this figure, the scope 100 includes the outer layer 102 and an inner layer 112, which together form a circumferential space 114 between the two. Again, in some embodiments, the outer diameter of the outer layer 102 may be less than 2 millimeters, or in some examples less than 1 millimeter. Multiple light fibers 110 (or "illumination fibers"), which transmit light from the light source 106 to the distal end 104 of the scope 100, may be positioned inside the circumferential space 114 (as illustrated), inside the central lumen 116, or both. Inside the inner layer 112 is a central lumen 116, which contains a camera module 118 and an optional elongate stiffening member 122. In this embodiment, the camera module 118 has a rectangular cross-sectional shape. In an alternative embodiment, the corners 120 of the camera module may be shaved, sanded or otherwise smoothed or rounded off.

As mentioned above, in some embodiments, the light fibers 110 are configured to emit visible light for illumination purposes and ultraviolet light, such as UVC light, for disinfecting the inside of a medical device. As UVC light can be highly caustic, it is important to transmit the light down the length of the light fibers 110 carefully, to prevent its unintended release. In some embodiments, each of the light fibers 110 may include a silica core, a doped silica clad, a polyimide layer, and a buffer made of polyimide, silicone, acrylate, fluoropolymer or other suitable buffer material. These are merely examples, however, and in alternative embodiments other materials or combinations may be used. In some embodiments, all the light fibers 110 may be configured to transmit visible light and UV light. In alternative embodiments, one set of fibers 110 may be configured to transmit visible light, and another set of fibers 110 may be configured to transmit UV light.

The stiffening member 122 is an optional component, used in some embodiments to enhance/increase the rigidity of the scope 100, to prevent over-bending or kinking. The stiffening member 122 may have any suitable size, length, shape and material, according to various embodiments. In some embodiments, for example, the stiffening member 122 may be a fiber, such as a glass or plastic fiber with a coating. In one embodiment, the stiffening member 122 may be a laser fiber, which in the scope 100 is not used for transmitting light but only as a piece to add rigidity to the scope 100.

In one embodiment, a method for making the medical device inspection scope 100 may involve positioning the inner layer 112 inside the outer layer 102, then placing the multiple light fibers 110 inside the circumferential space 114. The camera module 116 and laser fiber 122 may then be placed in the inner lumen 116 of the scope 100. In one example, the method of making the scope 100 may also include shaving, sanding or otherwise smoothing off corners 120 of the camera module 118.

A method for using the medical device inspection scope 100 may involve inserting the distal end 104 of the scope 100 into a lumen of a medical device, such as an endoscope, catheter or any other suitable device. The scope 100 is then advanced through the lumen, while the light fibers 110 are used to illuminate the lumen, and the camera module 116 is used to capture video and/or still images of the lumen. Some embodiments may include a processor for storing and/or interpreting data acquired by the camera module. For example, in some embodiments, the processor may be configured to identify irregularities or defects in the inside of an endoscope, catheter or other medical device.

The above description is intended to be a complete description of one embodiment of a small diameter endoscope for inspecting medical devices and potentially other uses. It is meant to be a description of examples only and is not intended to limit the scope of the invention.

We claim:

1. A cleaning and inspection scope for cleaning and inspecting of a medical device, the cleaning and inspection scope comprising:
   a cylindrical outer layer having a diameter of less than 2 millimeters;
   a single inner lumen disposed inside of the cylindrical outer layer, said inner lumen being the sole lumen within the cleaning and inspection scope;
   a camera module disposed in the inner lumen at a distal end of the cleaning and inspection scope, wherein the camera module is positioned entirely within the single inner lumen at the distal end of the cleaning and inspection scope;
   an illuminating light source;
   a disinfecting light source;
   multiple light transmitting fibers disposed in the inner lumen between the camera module and the outer layer, wherein the multiple light transmitting fibers are optically coupled to the illuminating light source and to the disinfecting light source to emit illuminating light for illuminating a field of view of the cleaning and inspection scope and ultraviolet light for disinfection of an inside of the medical device; and
   a stiffening member in the inner lumen for providing added stiffness to the cleaning and inspection scope.

2. The cleaning and inspection scope of claim 1, further comprising a light source positioned in proximity to a proximal end of the cleaning and inspection scope.

3. The cleaning and inspection scope of claim 1, wherein the camera module has a rectangular cross-sectional shape, and wherein the corners of the camera module are rounded off.

4. The cleaning and inspection scope of claim 1, wherein the cylindrical outer layer has a diameter of less than 1 millimeter.

5. The cleaning and inspection scope of claim 1, wherein the ultraviolet light comprises UVC light.

6. A method for making a cleaning and inspection scope for cleaning and inspecting of a medical device, the method comprising:
   providing a cylindrical outer layer having a diameter of less than 2 millimeters, a single inner lumen being disposed inside of the cylindrical outer layer;
   placing a camera module in the inner lumen at a distal end of the cleaning and inspection scope, wherein the camera module is positioned entirely within the single inner lumen at the distal end of the cleaning and inspection scope; and placing multiple light transmitting fibers in the inner lumen between the camera module and the outer layer, wherein the multiple light transmitting fibers are optically coupled to an illuminating light source configured to emit illuminating light for illuminating a field of view of the cleaning and inspection scope and to a disinfecting light source configured to emit ultraviolet light for disinfection of an inside of the medical device; and placing a stiffening member comprising a laser fiber in the inner lumen to provide added stiffness to the cleaning and inspection scope.

7. The method of claim 6, wherein the camera module has a rectangular cross-sectional shape, the method further comprising rounding off corners of the camera module.

8. The method of claim 6, wherein the cylindrical outer layer has a diameter of less than 1 millimeter.

9. The method of claim 6, wherein the ultraviolet light comprises UVC light.

10. A method for using the cleaning and inspection scope of claim 1, the method comprising:

advancing the cleaning and inspection scope into a lumen of a medical device;

emitting illuminating light from the multiple light transmitting fibers to illuminate the lumen of the medical device; and capturing an image of the lumen of the medical device with the camera module.

11. The method of claim 10, further comprising preventing the cleaning and inspection scope from kinking, using the stiffening member extending through the scope.

12. The method of claim 10, further comprising emitting ultraviolet light from the stiffening member for disinfecting the lumen of the medical device.

13. The method of claim 12, wherein the ultraviolet light comprises UVC light.

14. The method of claim 12, further comprising switching between emitting illuminating light and emitting ultraviolet light.

15. The method of claim 12, wherein the illuminating light and the ultraviolet light are emitted simultaneously.

16. The method of claim 12, wherein the medical device is selected from the group consisting of endoscopes and catheters.

* * * * *